(12) United States Patent
Hatada et al.

(10) Patent No.: US 9,297,745 B2
(45) Date of Patent: Mar. 29, 2016

(54) SHAPE MEASURING APPARATUS, AND METHOD OF MANUFACTURING ARTICLE

(71) Applicant: CANON KABUSHIKI KAISHA, Toyko (JP)

(72) Inventors: Akihiro Hatada, Utsunomiya (JP); Yoshiyuki Kuramoto, Utsunomiya (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/534,619

(22) Filed: Nov. 6, 2014

(65) Prior Publication Data

US 2015/0131096 A1    May 14, 2015

(30) Foreign Application Priority Data

Nov. 14, 2013   (JP) ................................ 2013-236264

(51) Int. Cl.
*G01J 4/00* (2006.01)
*G01N 21/21* (2006.01)
*G01B 11/25* (2006.01)

(52) U.S. Cl.
CPC ............ *G01N 21/21* (2013.01); *G01B 11/2513* (2013.01); *G01B 11/2527* (2013.01); *G01N 2201/061* (2013.01); *Y10T 29/49771* (2015.01)

(58) Field of Classification Search
USPC ........................................................ 356/364
See application file for complete search history.

(56) References Cited

U.S. PATENT DOCUMENTS 6,469,788 B2 * 10/2002 Boyd .................. G01N 21/211
356/369
2002/0012122 A1 * 1/2002 Boyd .................. G01N 21/211
356/369

FOREIGN PATENT DOCUMENTS

| EP | 2604972 A1 | 6/2013 |
| JP | 2005214787 A | 8/2005 |
| JP | 2007085753 A | 4/2007 |
| JP | 2013113581 A | 6/2013 |
| JP | 2013-178174 A | 9/2013 |

OTHER PUBLICATIONS

European search report issued in European counterpart application No. EP14190807.9, dated Mar. 31, 2015.

* cited by examiner

*Primary Examiner* — Roy M Punnoose
(74) *Attorney, Agent, or Firm* — Rossi, Kimms & McDowell LLP

(57) ABSTRACT

The present invention provides a measuring apparatus which measures a shape of an object to be measured, comprising an emitting unit configured to emit pattern light, an optical system configured to irradiate the object with the pattern light emitted from the emitting unit, a deflection unit configured to deflect light emitted from the optical system, an image sensing unit configured to sense an image of the object irradiated with the pattern light, and a processing unit configured to determine the shape of the object based on the image of the object sensed by the image sensing unit, wherein the deflection unit includes a deflection element, wherein the measuring apparatus irradiates the object with light deflected by the deflection element, and a direction deflected by the deflection element differs depending on a polarization state of incident light in the deflection element.

12 Claims, 4 Drawing Sheets

SHAPE MEASURING APPARATUS, AND METHOD OF MANUFACTURING ARTICLE

BACKGROUND OF THE INVENTION

1. Field of the Invention

The present invention relates to a measuring apparatus which measures the shape of an object, and a method of manufacturing an article.

2. Description of the Related Art

As a method of measuring the shape of an object using light in a noncontact manner, a pattern projection method (pattern projection triangulation) is known. The pattern projection method is a method of obtaining the shape of an object to be measured by sensing an image of the object to which a known two-dimensional pattern has been projected, and detecting the deformation amount of the two-dimensional pattern generated in accordance with the shape of the object.

In general, a measuring apparatus using the pattern projection method individually includes a projection optical system for projecting pattern light to an object to be measured, and an imaging optical system for sensing an image of the object irradiated with the pattern light. To measure the shape of an object at high accuracy in the measuring apparatus using the pattern projection method, it is effective to constitute the projection optical system and imaging optical system as telecentric optical systems.

Japanese Patent Laid-Open No. 2013-178174 has disclosed a method of enlarging a measurement range by exploiting the difference in the phase period of a grating pattern image to be sensed using a whole-space tabulation method.

The measuring apparatus using the pattern projection method desirably has a wide field of view and a wide measurement range in the direction of height in order to improve the throughput. To achieve both the wide field of view and the wide measurement range, measures such as widening of the field of view of the projection optical system or imaging optical system, and decreasing of the the convergence angle are conceivable. However, to widen the field of view of the optical system, the size of the optical system needs to be increased because the optical system is telecentric. This increases the apparatus size and apparatus cost. If the convergence angle is decreased, the working distance may need to be prolonged in order to avoid physical interference between the projection optical system and the imaging optical system. This may upsize the measuring apparatus.

The method disclosed in Japanese Patent Laid-Open No. 2013-178174 requires a high-accuracy driving mechanism of finely driving an object to be measured in the direction of height. This complicates the apparatus and raises the apparatus cost. Since the object needs to be measured while finely driving it, a long measurement time is taken.

SUMMARY OF THE INVENTION

The present invention provides, for example, a technique advantageous for implementing a wide field of view, a wide measurement range, and downsizing in a measuring apparatus which measures the shape of an object by the pattern projection method.

According to one aspect of the present invention, there is provided a measuring apparatus which measures a shape of an object to be measured, comprising: an emitting unit configured to emit pattern light; an optical system configured to irradiate the object with the pattern light emitted from the emitting unit; a deflection unit configured to deflect light emitted from the optical system; an image sensing unit configured to sense, through the optical system and the deflection unit, an image of the object irradiated with the pattern light; and a processing unit configured to determine the shape of the object based on the image of the object sensed by the image sensing unit, wherein the deflection unit includes a deflection element, wherein the measuring apparatus irradiates the object with light deflected by the deflection element, and a direction deflected by the deflection element differs depending on a polarization state of incident light in the deflection element.

Further features of the present invention will become apparent from the following description of exemplary embodiments with reference to the attached drawings.

DESCRIPTION OF THE EMBODIMENTS

Figure 1:
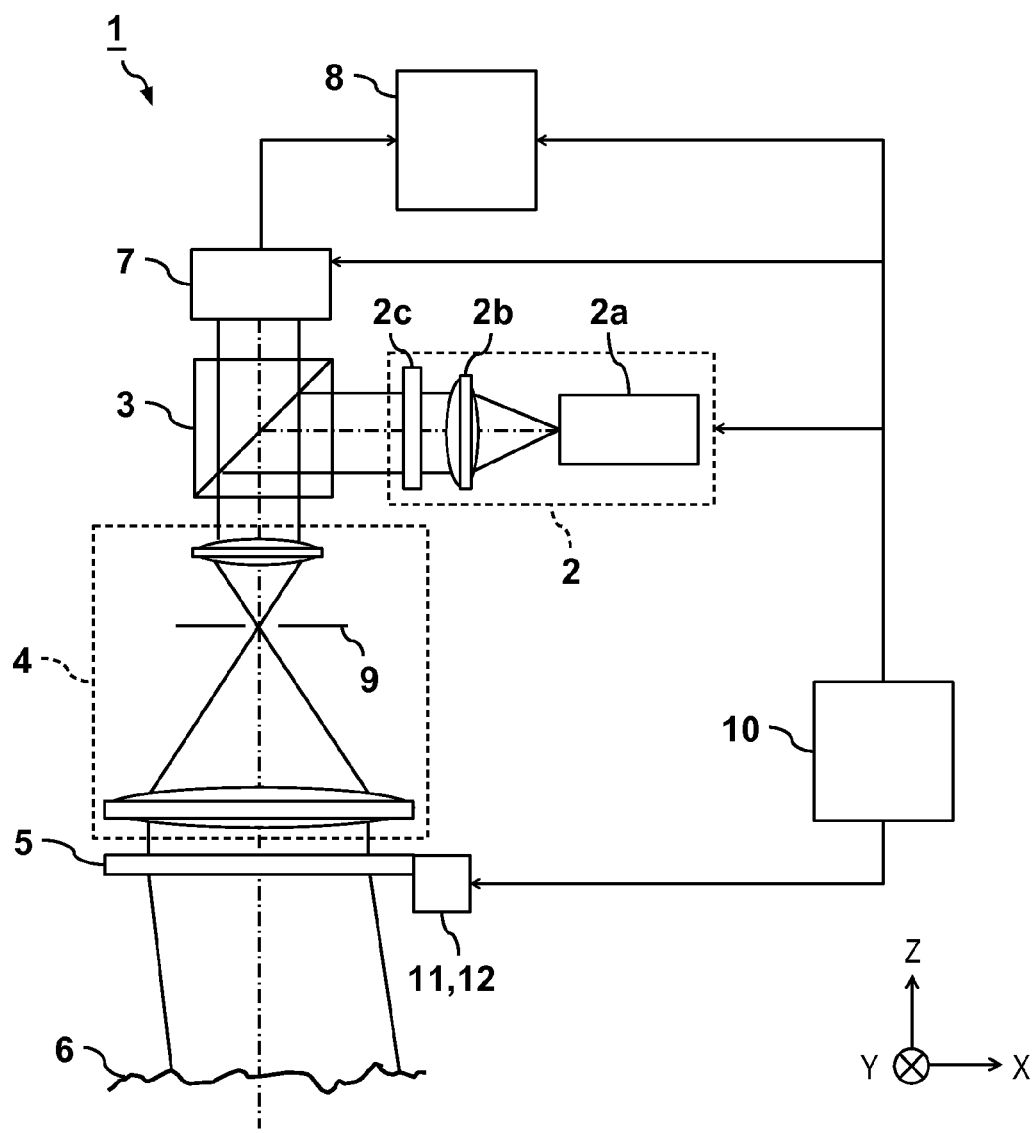
FIG. 1 is a schematic view showing a measuring apparatus according to the first embodiment.

Exemplary embodiments of the present invention will be described below with reference to the accompanying drawings. Note that the same reference numerals denote the same members throughout the drawings, and a repetitive description thereof will not be given.

First Embodiment

A measuring apparatus 1 according to the first embodiment of the present invention will be described with reference to FIG. 1. The measuring apparatus 1 according to the first embodiment adopts a pattern projection method (pattern projection triangulation) of obtaining the shape of an object 6 to be measured by sensing an image of the object 6 to which a pattern whose bright and dark portions periodically change has been projected, and detecting the deformation amount of the pattern generated in accordance with the shape of the object 6. The pattern projection method includes several methods for measuring the shape of the object 6, such as a phase shift method and space encoding method. Above all, the phase shift method is a method of sensing an image of the object 6 to which a sinusoidal pattern has been projected while shifting the phase of the sinusoidal pattern by every predetermined angle, and then obtaining the shape of the object based on a change of the received light intensity in each pixel of the sensed image. The phase shift method has high measurement accuracy. The first embodiment will explain a method of measuring the shape of the object 6 by using the phase shift method. The measuring apparatus 1 according to the first embodiment uses an optical system 4 in which a projection optical system and imaging optical system are shared at least partially. In order to generate a convergence angle α, a deflection unit 5 configured to deflect pattern light emitted from the optical system 4 is arranged. With this arrangement, both widening of the measurement range and field of view of the measuring apparatus, and downsizing of the measuring apparatus can be achieved. In addition, the shape of an object can be measured at the convergence angle α at high accuracy. The arrangement of the measuring apparatus 1 according to the first embodiment will be explained below.

FIG. 1 is a schematic view showing the measuring apparatus 1 according to the first embodiment. The measuring apparatus 1 according to the first embodiment can include an emitting unit 2, a polarizing beam splitter 3, the optical system 4, the deflection unit 5, an image sensing unit 7, a processing unit 8, and a control unit 10. The processing unit 8 is constituted by, for example, a computer including a CPU, memory, and the like. Based on the image of the object 6 sensed by the image sensing unit 7, the processing unit 8 determines the shape of the object 6. The control unit 10 includes a CPU, memory, and the like, and controls measurement of the object 6 (controls each unit of the measuring apparatus 1).

The emitting unit 2 can include, for example, a light source 2a, collimator lens 2b, and conversion element 2c. The light source 2a emits light having a predetermined polarization direction. Light emitted from the light source 2a is collimated into parallel light by the collimator lens 2b, is incident on the conversion element 2c, and is converted by the conversion element 2c into pattern light whose bright and dark portions periodically change. The conversion element 2c may include, for example, a mask having a pattern in which light-transmissive portions and light-shielding portions are arranged periodically (alternately). The conversion element 2c can include a liquid crystal element, digital mirror device (DMD), and the like. This is because light emitted from the light source 2a can be converted into, for example, light (pattern light) having an arbitrary pattern such as a monochrome pattern or sinusoidal pattern. Since the liquid crystal element and DMD can perform spatial modulation at a high speed, mechanical driving when shifting the pattern phase in the phase shift method becomes unnecessary, which is advantageous for improving the throughput.

Pattern light having passed through the conversion element 2c is reflected by the polarizing beam splitter 3, and is incident on the optical system 4. The optical system 4 includes, for example, two lenses for enlarging the diameter of pattern light, and an aperture stop 9 arranged at a condensing position between the two lenses. The pattern light having passed through the optical system 4 is deflected by the deflection unit 5, and irradiates the surface of the object 6. The wavelength of the pattern light is set to be shorter than the surface roughness of the object 6. Thus, the pattern light irradiating the surface of the object 6 is diffusedly reflected scattered on the object surface. The pattern light reflected by the surface of the object 6 is incident on the optical system 4 through the deflection unit 5. After the spatial frequency of the pattern light is narrowed by the aperture stop 9 of the optical system 4, the pattern light passes through the polarizing beam splitter 3, and is incident on the image sensing unit 7. The image sensing unit 7 includes, for example, a CCD sensor or CMOS sensor, and senses, through the optical system 4, an image of the object 6 irradiated with the pattern light.

Figure 2:
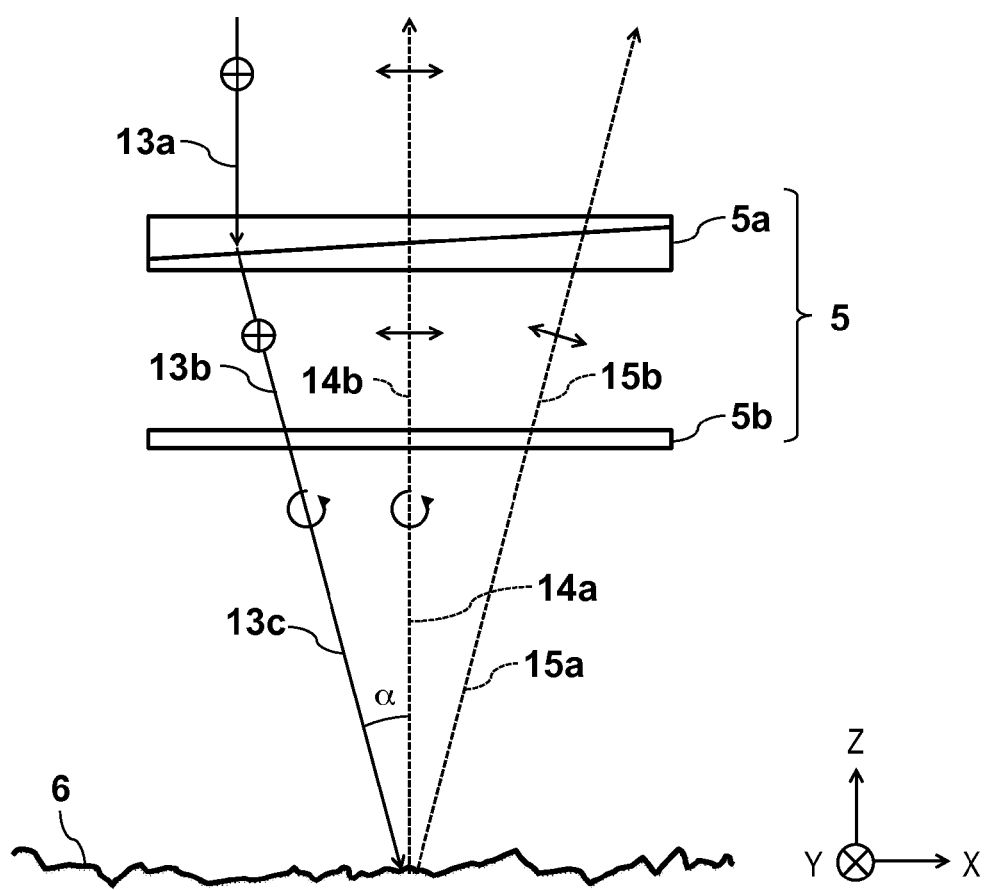
FIG. 2 is a schematic view showing the arrangement of a deflection unit according to the first embodiment.

The arrangement and function of the deflection unit 5 will be described with reference to FIG. 2. FIG. 2 is a schematic view showing the arrangement of the deflection unit 5 according to the first embodiment. The deflection unit 5 includes a deflection element in which the deflection direction changes depending on the polarization state of incident light, and a λ/4 waveplate 5b interposed between the deflection element and an object (on the light exit side of the deflection element). The first embodiment will explain a case in which the deflection element includes a polarizing prism 5a. The polarizing prism 5a is configured so that the deflection direction of pattern light emitted from the optical system 4 and the deflection direction of pattern light reflected by the object 6 differ from each other. As the polarizing prism 5a, a Wollaston prism, Rochon prism, saber plate, or the like is usable. The deflection element may be inserted in the optical path of parallel light emitted from the optical system 4. Note that an optical member may be arranged on the light exit side of the deflection element.

For example, assume that pattern light 13a having the Y polarization direction is emitted from the optical system 4, and is incident on the polarizing prism 5a, as shown in FIG. 2. In this case, the pattern light 13a emitted from the optical system 4 passes through the polarizing prism 5a, and is deflected to be pattern light 13b shown in FIG. 2. The pattern light 13b is incident on the λ/4 waveplate 5b. The λ/4 waveplate 5b is configured to rotate the fast axis by 45° with respect to the direction of linearly polarized light incident on the λ/4 waveplate 5b. Thus, pattern light 13c having passed through the λ/4 waveplate 5b becomes circularly polarized light, which irradiates the surface of the object 6. Of the light reflected (scattered) by the surface of the object 6, pattern light 14a reflected in a direction (optical axis direction (Z direction)) parallel to the optical axis of the optical system 4 passes again through the λ/4 waveplate 5b. The pattern light 14a is then changed into pattern light 14b which has been rotated by 90° with respect to the pattern light 13a emitted from the optical system 4 and has the X polarization direction. The pattern light 14b travels straight without being deflected by the polarizing prism 5a, passes through the polarizing beam splitter 3 without being cut by the aperture stop 9 of the optical system 4, and is incident on the image sensing unit 7. Although polarization is rotated using the waveplate in the embodiment, the waveplate is not always necessary when, for example, a change of polarization by scattering on an object is sufficiently large.

Of the light reflected (scattered) by the surface of the object 6, pattern light 15a reflected in a direction different from the optical axis direction is incident again on the λ/4 waveplate 5b similarly to the pattern light 14a reflected in the optical axis direction. The pattern light 15a passes again through the λ/4 waveplate 5b, and is changed into pattern light 15b which has been rotated by 90° with respect to the pattern light 13a emitted from the optical system 4 and has the X polarization direction. Hence, the pattern light 15b travels straight without being deflected by the polarizing prism 5a. However, the pattern light 15b having passed through the polarizing prism 5a travels in a direction different from the optical axis direction, is cut by the aperture stop 9 of the optical system 4, and is not incident on the image sensing unit 7.

Figure 3:
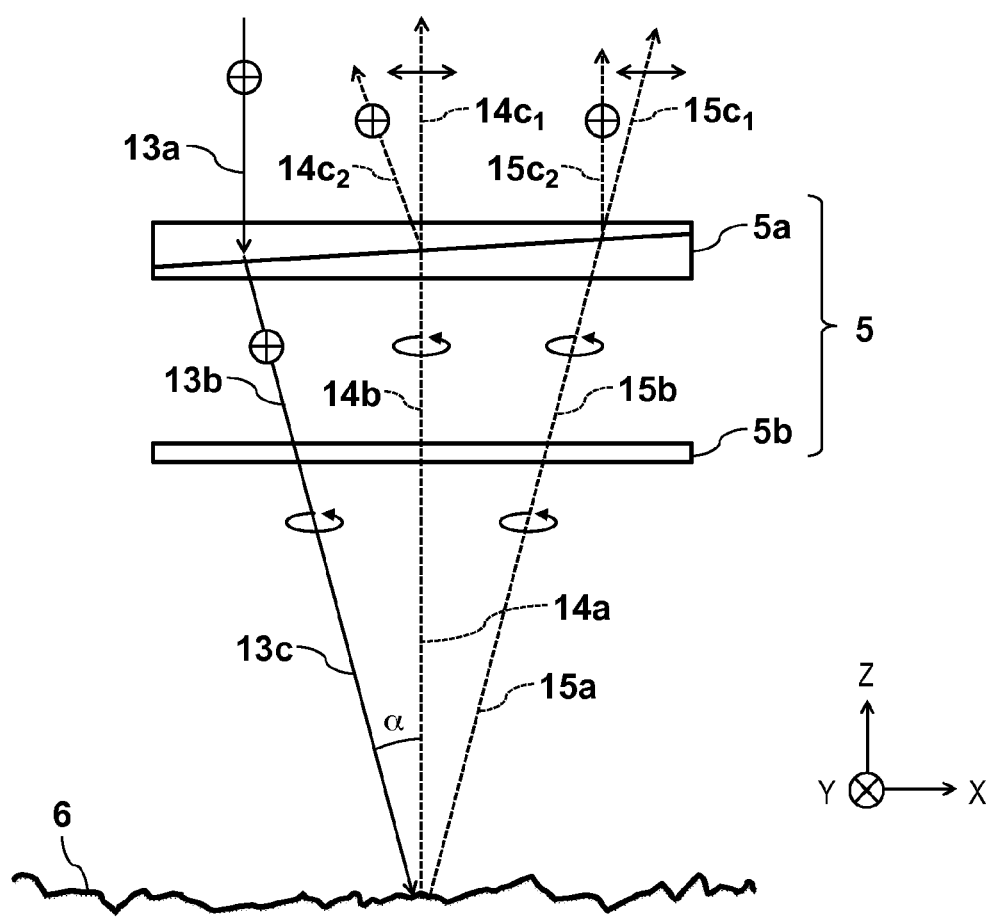
FIG. 3 is a schematic view showing the arrangement of the deflection unit according to the first embodiment.

When the deflection unit 5 has an optical characteristic error (polarization error), the pattern light 15a reflected in a direction different from the optical axis direction by the object 6 may be deflected in the optical axis direction by the polarizing prism 5a. Even in this case, the measuring apparatus 1 according to the first embodiment can cause the pattern light 14a reflected in the optical axis direction by the surface of the object 6 to be incident on the image sensing unit 7, and limit the incidence, on the image sensing unit 7, of the pattern light 15a reflected in a direction different from the optical axis direction by the surface of the object 6. FIG. 3 is a view for explaining the arrangement and function of the deflection unit 5 when the deflection unit 5 has the polarization error. The pattern light 13c emitted from the optical system 4 and having passed through the deflection unit 5 (λ/4 waveplate 5b) becomes elliptic polarization owing to the polarization error of the deflection unit 5, particularly, a retardation error generated when light is obliquely incident on the λ/4 waveplate 5b. For this reason, the pattern light 14a reflected in the optical axis direction by the surface of the object 6, and the pattern light 15a reflected in a direction different from the optical axis direction become not linearly polarized light but elliptic polarization even after passing again through the λ/4 waveplate 5b.

The pattern light 14b reflected in the optical axis direction by the surface of the object 6 and having passed through the λ/4 waveplate 5b passes through the polarizing prism 5a, and is separated into pattern light $14c_1$ having the X polarization direction, and pattern light $14c_2$ having the Y polarization direction. The pattern light $14c_1$ having the X polarization direction travels in the optical axis direction without being deflected by the polarizing prism 5a, passes through the polarizing beam splitter 3 without being cut by the aperture stop 9 of the optical system 4, and is incident on the image sensing unit 7. In contrast, the pattern light $14c_2$ having the Y polarization direction is deflected by the polarizing prism 5a, and travels in a direction different from the optical axis direction. Thus, the pattern light $14c_2$ is cut by the aperture stop 9 of the optical system 4, and is not incident on the image sensing unit 7.

The pattern light 15b reflected in a direction different from the optical axis direction by the surface of the object 6 and having passed through the λ/4 waveplate 5b passes through the polarizing prism 5a, and is separated into pattern light $15c_1$ having the X polarization direction and pattern light $15c_2$ having the Y polarization direction. The pattern light $15c_1$ having the X polarization direction travels in a direction different from the optical axis direction without being deflected by the polarizing prism 5a, is cut by the aperture stop 9 of the optical system 4, and is not incident on the image sensing unit 7. To the contrary, the pattern light $15c_2$ having the Y polarization direction is deflected by the polarizing prism 5a, travels in the optical axis direction, and may be incident on the polarizing beam splitter 3 without being cut by the aperture stop 9 of the optical system 4. However, the pattern light $15c_2$ having the Y polarization direction is reflected by the polarizing beam splitter 3, and is not incident on the image sensing unit 7. Therefore, even when the polarization error is generated in the deflection unit 5, the measuring apparatus 1 according to the first embodiment can cause the pattern light 14a reflected in the optical axis direction by the surface of the object 6 to be incident on the image sensing unit 7. In addition, the measuring apparatus 1 according to the first embodiment can limit the incidence, on the image sensing unit 7, of the pattern light 15a reflected in a direction different from the optical axis direction by the surface of the object 6.

As described above, the measuring apparatus 1 according to the first embodiment includes the polarizing prism 5a and λ/4 waveplate 5b. This makes it possible to at least partially share the projection optical system and imaging optical system. Since the convergence angle α can be generated in accordance with the deflection angle of the polarizing prism 5a, pattern light reflected at the convergence angle α with respect to pattern light irradiating the surface of the object 6 can be incident on the image sensing unit 7. That is, the measuring apparatus 1 according to the first embodiment can achieve both widening of the measurement range and field of view of the measuring apparatus, and downsizing of the measuring apparatus, and can measure the shape of the object 6 at the convergence angle α at high accuracy. The deflection angle (convergence angle α) of the polarizing prism 5a can be determined based on the difference in refractive index between two glass materials constituting the polarizing prism 5a, the angle at the interface between the two glass materials, and the like.

Next, processing to be performed by the processing unit 8 to determine the shape of the object 6 will be explained. The processing unit 8 is constituted by, for example, a computer including a CPU, memory, and the like. The processing unit 8 determines the shape of the object 6 based on the image of the object 6 sensed by the image sensing unit 7. The processing unit 8 calculates a phase in each pixel based on a change of the received light intensity in each pixel of an image sensed while the conversion element 2c shifts the phase of a pattern projected to the surface of the object 6. For example, the pattern phase is shifted N times by Δφ at a point P of coordinates (x, y) on the surface of the object 6. Discrete Fourier transform (DFT) is performed for a received light intensity $I_k(x, y)$ for each phase. A phase θ(x, y) at the point P can be obtained by:

$$\theta(x, y) = \tan^{-1} \left( \frac{\sum_{k=0}^{N-1} I_k(x, y) \cdot \sin(\Delta\phi \times k)}{\sum_{k=0}^{N-1} I_k(x, y) \cdot \cos(\Delta\phi \times k)} \right) \quad (1)$$

By applying the triangulation principle based on the obtained phase θ(x, y), the shape of the object 6 can be determined.

As shown in FIG. 1, the measuring apparatus 1 according to the first embodiment may include a driving unit 11 (second driving unit) which rotates the deflection element (polarizing prism 5a) around the optical axis of the optical system 4. By rotating the deflection unit 5 around the optical axis of the optical system 4 by the driving unit 11, the angle at which pattern light emitted from the deflection unit 5 irradiates the surface of the object 6 can be changed. This can reduce generation of a portion (unmeasurable blind spot) not irradiated with pattern light owing to the roughness of the object 6. In the measuring apparatus 1 according to the first embodiment, for example, a diffraction element which is used in a 3D display to separate incident light into beams of left and right circularly polarized light components can also be used as the deflection element, other than the polarizing prism 5a. The diffraction grating for the 3D display has a function of changing the deflection direction in accordance with the polarization state of incident light. By arranging a λ/4 waveplate at a subsequent stage, the deflection direction of light can be changed between the forward path and the return path.

Second Embodiment

A measuring apparatus according to the second embodiment of the present invention will be described with reference to FIG. 4. The measuring apparatus according to the second embodiment is different from the measuring apparatus 1 according to the first embodiment in the arrangement of a deflection unit 5. A polarization diffraction grating 5c is used as the deflection element. The measuring apparatus according to the second embodiment has the same apparatus arrangement as that of the measuring apparatus 1 according to the first embodiment except for the deflection unit 5, and a description of the apparatus arrangement except for the deflection unit 5 will not be repeated.

Figure 4:
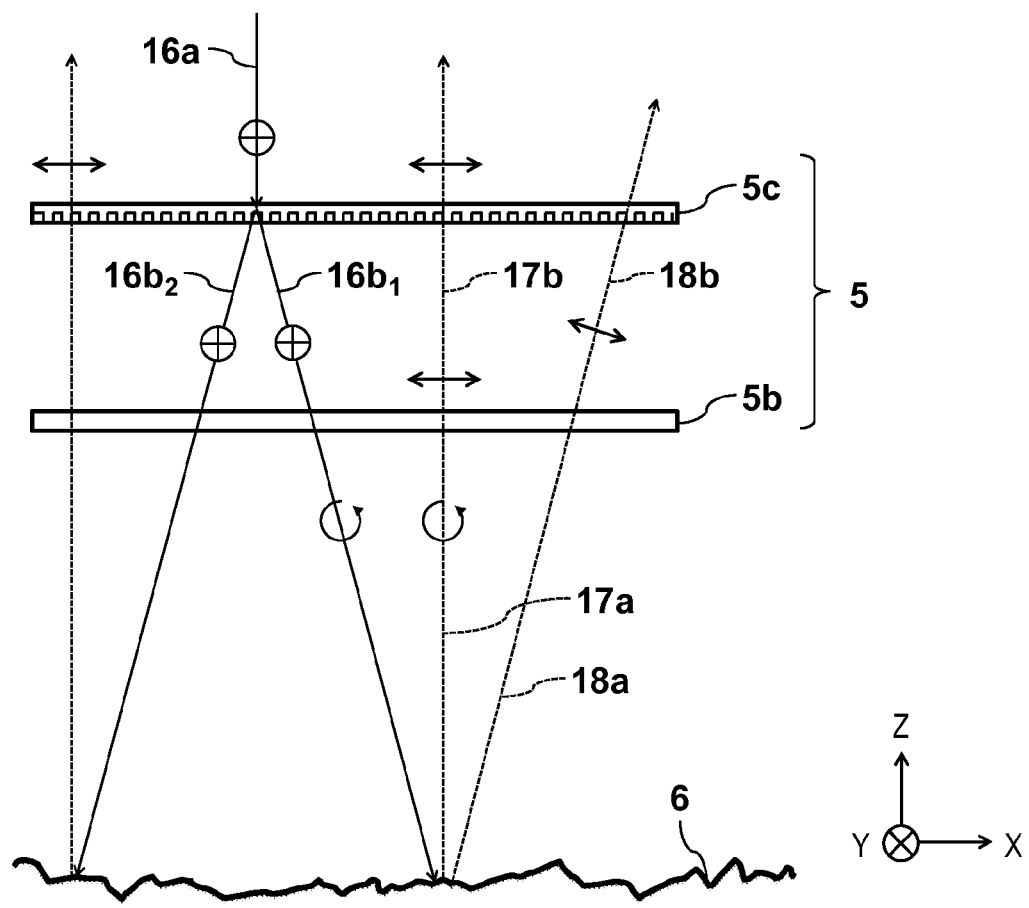
FIG. 4 is a schematic view showing the arrangement of a deflection unit according to the second embodiment.

FIG. 4 is a schematic view showing the arrangement of the deflection unit 5 according to the second embodiment. The second embodiment will explain a case in which the deflection element includes the polarization diffraction grating 5c. The polarization diffraction grating 5c is a diffraction grating formed from, for example, a photo-alignment film or liquid crystal polymer film. The polarization diffraction grating 5c has a characteristic in which the traveling direction (deflection direction) of incident light changes depending on the polarization state of the light. In other words, the polarization diffraction grating 5c operates as a diffraction grating in a predetermined polarization state, but does not operate as a diffraction grating in a polarization state rotated by 90° from the predetermined polarization state. In FIG. 4, pattern light 16a emitted from an optical system 4 has a polarization state (Y polarization direction) in which the polarization diffraction grating 5c operates as a diffraction grating. The polarization diffraction grating 5c separates the pattern light 16a into +1st-order diffracted light 16b$_1$ and −1st-order diffracted light 16b$_2$. The +1st-order diffracted light 16b$_2$ and −1st-order diffracted light 16b$_2$ pass through a λ/4 waveplate 5b, and are changed into circularly polarized beams to irradiate an object to be measured.

Of the +1st-order diffracted light 16b$_2$ reflected (scattered) by the surface of an object 6 to be measured, light 17a reflected in the optical axis direction passes again through the λ/4 waveplate 5b, and is changed into light 17b which has been rotated by 90° with respect to the pattern light 16a emitted from the optical system 4 and has the X polarization direction. The light 17b travels straight without being deflected by the polarization diffraction grating 5c, passes through a polarizing beam splitter 3 without being cut by an aperture stop 9 of the optical system 4, and is incident on an image sensing unit 7. In contrast, of the +1st-order diffracted light 16b$_2$ reflected (scattered) by the surface of the object 6, light 18a reflected in a direction different from the optical axis direction passes again through the λ/4 waveplate 5b similarly to the light 17a reflected in the optical axis direction. The light 18a is then changed into light 18b which has been rotated by 90° with respect to the pattern light 16a emitted from the optical system 4 and has the X polarization direction. Hence, the light 18b travels straight without being deflected by the polarization diffraction grating 5c. However, the light having passed through the polarization diffraction grating 5c travels in a direction different from the optical axis direction, is cut by the aperture stop 9 of the optical system 4, and is not incident on the image sensing unit 7. Note that the behavior of the −1st-order diffracted light 16b$_2$ is the same as that of the +1st-order diffracted light 16b$_1$, and a description thereof will not be repeated.

In the second embodiment, an image sensed by the image sensing unit 7 is an image in which a pattern image formed by +1st-order diffracted light and a pattern image formed by −1st-order diffracted light overlap each other. Thus, the pattern image formed by +1st-order diffracted light and the pattern image formed by −1st-order diffracted light may be separated by the processing unit 8. However, the respective overlapping pattern images are modulated in the same amount in the same direction only by modulation of pattern light by the conversion element 2c, so it may be difficult to separate these pattern images. It is therefore desirable to apply different phase shift amounts to +1st-order diffracted light and −1st-order diffracted light. In this case, by performing discrete Fourier transform based on each phase shift amount, it becomes possible to obtain the phase of each pixel based on a change of the received light intensity in each pixel of an image sensed by the image sensing unit 7, and determine the shape of the object.

One method of applying different phase shift amounts to +1st-order diffracted light and −1st-order diffracted light is a method of moving the deflection unit 5 in the optical axis direction. For this purpose, the measuring apparatus according to the second embodiment may include a driving unit 12 (first driving unit) which drives the deflection element (polarization diffraction grating 5c) in the optical axis direction (Z direction), as shown in FIG. 1. When the driving unit 12 drives the deflection unit 5 in the optical axis direction, the phase of +1st-order diffracted light and the phase of −1st-order diffracted light change in opposite directions. Thus, by a combination of driving of the deflection unit 5 by the driving unit 12, and modulation of pattern light by the conversion element 2c, the phase of +1st-order diffracted light and the phase of −1st-order diffracted light can be changed individually and arbitrarily. For example, by combining, by a conversion unit, phase shifts of 3π/5, and π/5, which is ⅒ of the wavelength of light passing through the polarization diffraction grating, different phase shift amounts of 2π/5 and 4π/5 can be applied to +1st-order diffracted light and −1st-order diffracted light. The driving unit 12 in the measuring apparatus according to the second embodiment may have a function (function of the second driving unit) of rotating the deflection element (polarization diffraction grating 5c) around the optical axis of the optical system 4. This can reduce a portion (unmeasurable blind spot) not irradiated with pattern light owing to the roughness of the object 6.

As described above, the measuring apparatus according to the second embodiment includes the polarization diffraction grating 5c and λ/4 waveplate 5b. Similarly to the measuring apparatus 1 according to the first embodiment, the measuring apparatus according to the second embodiment can achieve both widening of the measurement range of the measuring apparatus and downsizing of the measuring apparatus, and can measure the shape of the object 6 at high accuracy.

<Embodiment of Method of Manufacturing Article>

A method of manufacturing an article according to an embodiment of the present invention is used to manufacture an article such as a metal part or optical element. The method of manufacturing an article according to the embodiment includes a step of measuring the shape of an object using the measuring apparatus, and a step of processing the object based on the measuring result in the preceding step. For example, the shape of an object is measured using the measuring apparatus, and the object is processed (manufactured) based on the measuring result so that the shape of the object matches the design value. The method of manufacturing an article according to the embodiment can measure the shape of an object by the measuring apparatus at high accuracy, and thus is superior to a conventional method in at least one of the performance, quality, productivity, and production cost of the article.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-236264 filed Nov. 14, 2013, which is hereby incorporated by reference herein in its entirety.

What is claimed is:

1. A measuring apparatus which measures a shape of an object to be measured, comprising:
   an emitting unit configured to emit pattern light;
   an optical system configured to irradiate the object with the pattern light emitted from the emitting unit;
   a deflection unit configured to deflect light emitted from the optical system;
   an image sensing unit configured to sense, through the optical system and the deflection unit, an image of the object irradiated with the pattern light; and a processing unit configured to determine the shape of the object based on the image of the object sensed by the image sensing unit, wherein the deflection unit includes a deflection element, wherein the measuring apparatus irradiates the object with light deflected by the deflection element, and a direction deflected by the deflection element differs depending on a polarization state of incident light in the deflection element.

2. The apparatus according to claim 1, wherein the deflection element includes a polarizing prism.

3. The apparatus according to claim 1, wherein the deflection element includes a polarization diffraction grating.

4. The apparatus according to claim 1, wherein the optical system includes an aperture stop which is configured to transmit light reflected in a direction parallel to an optical axis of the optical system, of the pattern light reflected by a surface of the object.

5. The apparatus according to claim 1, further comprising a polarizing beam splitter which is configured to guide the pattern light which is emitted from the emitting unit, to the optical system, and guide the pattern light which is reflected by the surface of the object and having passed through the optical system, to the image sensing unit.

6. The apparatus according to claim 1, further comprising a first driving unit configured to drive the deflection element in a direction parallel to the optical axis of the optical system.

7. The apparatus according to claim 1, further comprising a second driving unit configured to rotate the deflection element around the optical axis of the optical system.

8. The apparatus according to claim 1, wherein the emitting unit includes a light source, and a conversion element configured to convert light emitted from the light source into the pattern light.

9. The apparatus according to claim 8, wherein the conversion element includes at least one of a mask having a pattern in which light-transmissive portions and light-shielding portions are alternately arranged, a liquid crystal element, and a digital mirror device.

10. The apparatus according to claim 1, wherein the deflection unit includes a waveplate arranged on a light exit side of the deflection element.

11. The apparatus according to claim 1, wherein the polarization state is a polarization direction.

12. A method of manufacturing an article, the method comprising:

measuring a shape of an object using a measuring apparatus; and processing the object based on a measuring result in the measuring, wherein the measuring apparatus includes:

an emitting unit configured to emit pattern light;

an optical system configured to irradiate the object with the pattern light emitted from the emitting unit;

a deflection unit configured to deflect light emitted from the optical system;

an image sensing unit configured to sense, through the optical system and the deflection unit, an image of the object irradiated with the pattern light; and a processing unit configured to determine the shape of the object based on the image of the object sensed by the image sensing unit, wherein the deflection unit includes a deflection element, wherein the measuring apparatus irradiates the object with light deflected by the deflection element, and a direction deflected by the deflection element differs depending on a polarization state of incident light in the deflection element.

* * * * *